(12) United States Patent
Adell et al.

(10) Patent No.: US 7,201,575 B2
(45) Date of Patent: Apr. 10, 2007

(54) DENTAL APPLIANCE AND METHOD FOR MAKING

(76) Inventors: Loren S. Adell, 52 Armstrong Dr., Frisco, TX (US) 75034-1859; Michael L. Adell, 2627 Woods La., Garland, TX (US) 75044-2805

(\*) Notice: Subject to any disclaimer, the term of this patent is extended or adjusted under 35 U.S.C. 154(b) by 0 days.

(21) Appl. No.: 11/114,446

(22) Filed: Apr. 26, 2005

(65) Prior Publication Data
US 2005/0244793 A1 Nov. 3, 2005

(51) Int. Cl.
*A61C 7/00* (2006.01)
*A61C 17/02* (2006.01)

(52) U.S. Cl. .............................. 433/6; 433/80; 433/213
(58) Field of Classification Search .................... 433/6, 433/213, 80
See application file for complete search history.

(56) References Cited

U.S. PATENT DOCUMENTS 6,077,075 A \* 6/2000 Bedard et al. .............. 433/167
6,638,496 B2 \* 10/2003 McLaughlin ................ 424/53

\* cited by examiner

*Primary Examiner*—Cary E. O'Connor
(74) *Attorney, Agent, or Firm*—W. Thomas Timmons

(57) ABSTRACT

A method for making a dental appliance is disclosed, including affixing a first blank piece of material to a second blank piece of material forming a combined blank. The first blank piece of material is substantially softer than the second blank piece of material. The combined blank is then placed over a dental cast with the first blank piece of material faces the dental cast, and a dental appliance is formed by using a thermal form suck-down of the combined blank over the dental cast with the first blank piece of material in contact with the teeth of the dental cast. Finally, the dental appliance is removed from the dental cast. The dental appliance can be trimmed while it is on the dental cast or after it is removed. Methods for affixing a first blank piece of material to a second blank piece of material, include laminating the first blank piece of material to the second blank piece of material, bonding the first blank piece of material to the second blank piece of material, and sealing the first blank piece of material to the second blank piece of material. A dental appliance for placement on the teeth of a user is disclosed, including a first layer, created from the first piece of blank material, for direct contact with the teeth of the user, and a second layer, created from the second piece of blank material, affixed over the first layer. The first layer is substantially softer than the second layer.

12 Claims, 5 Drawing Sheets

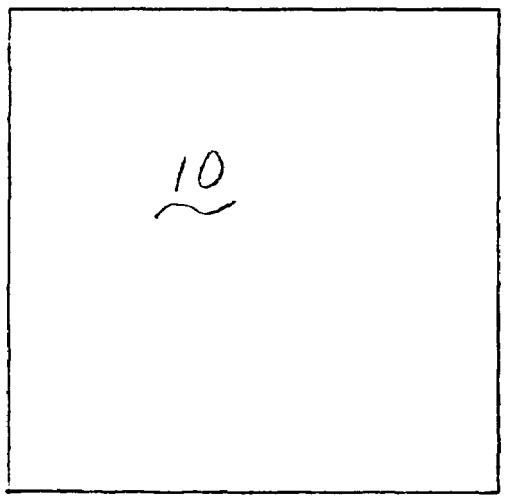
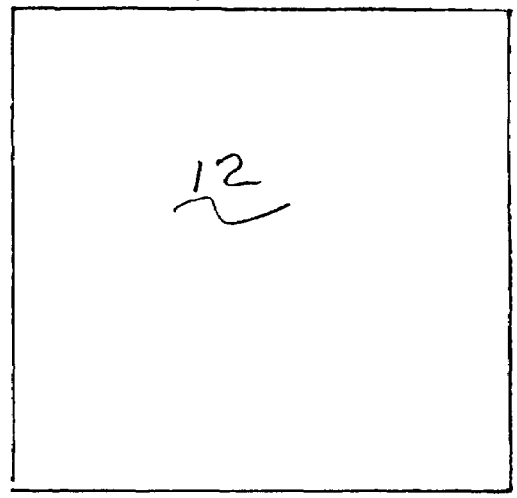
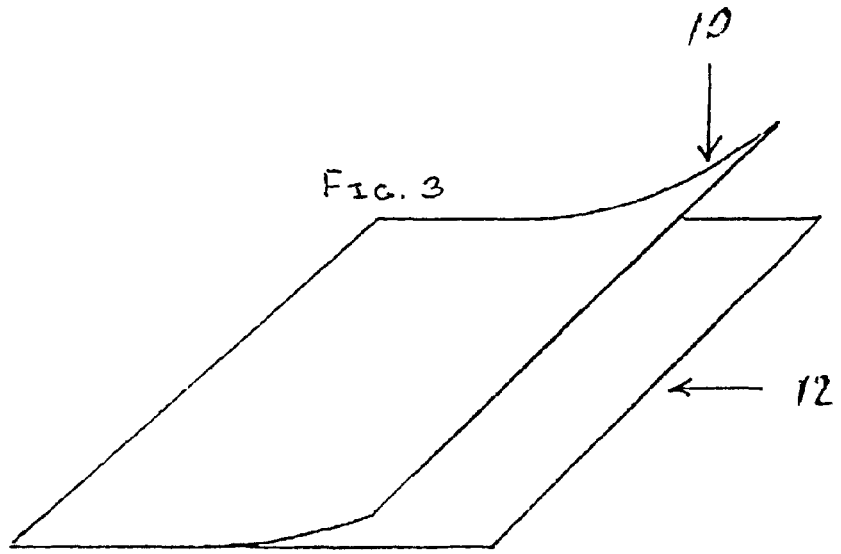
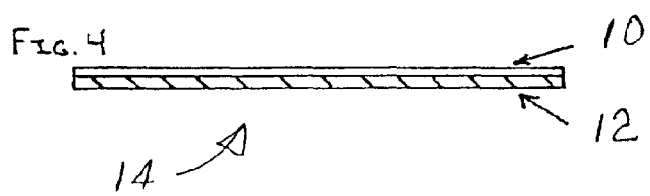

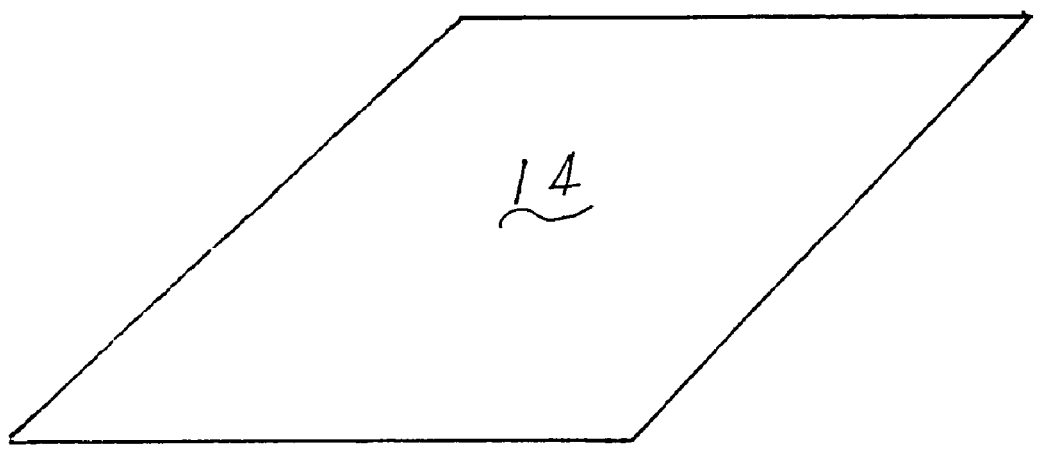
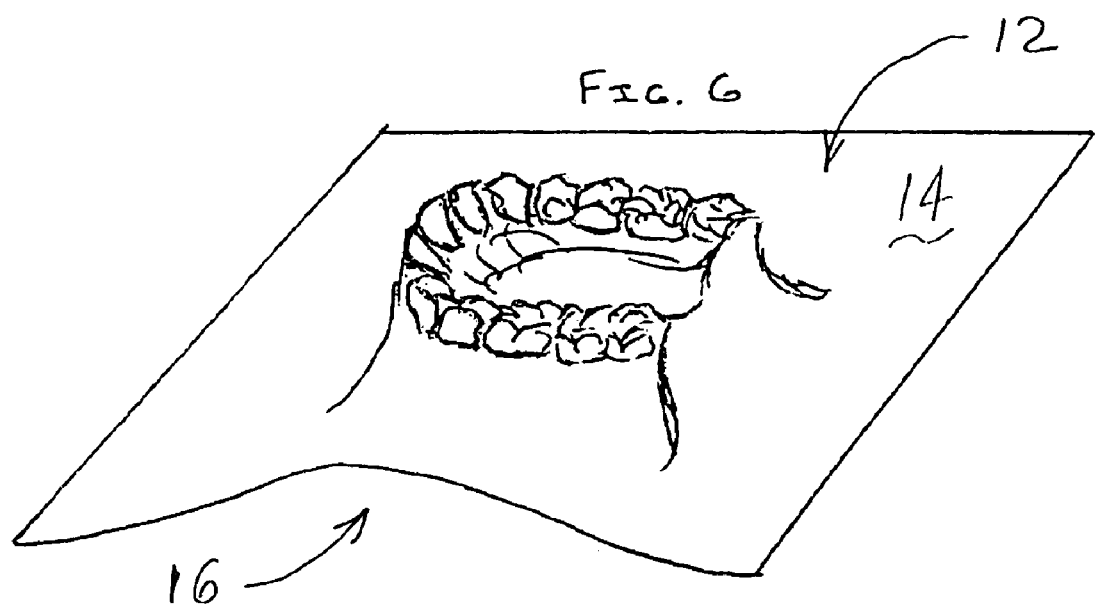

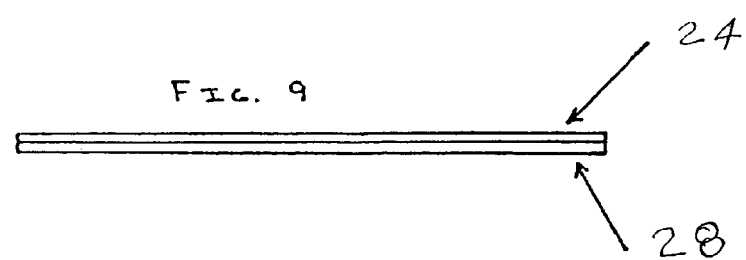
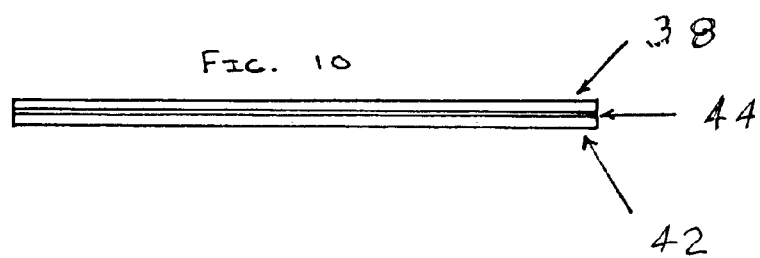
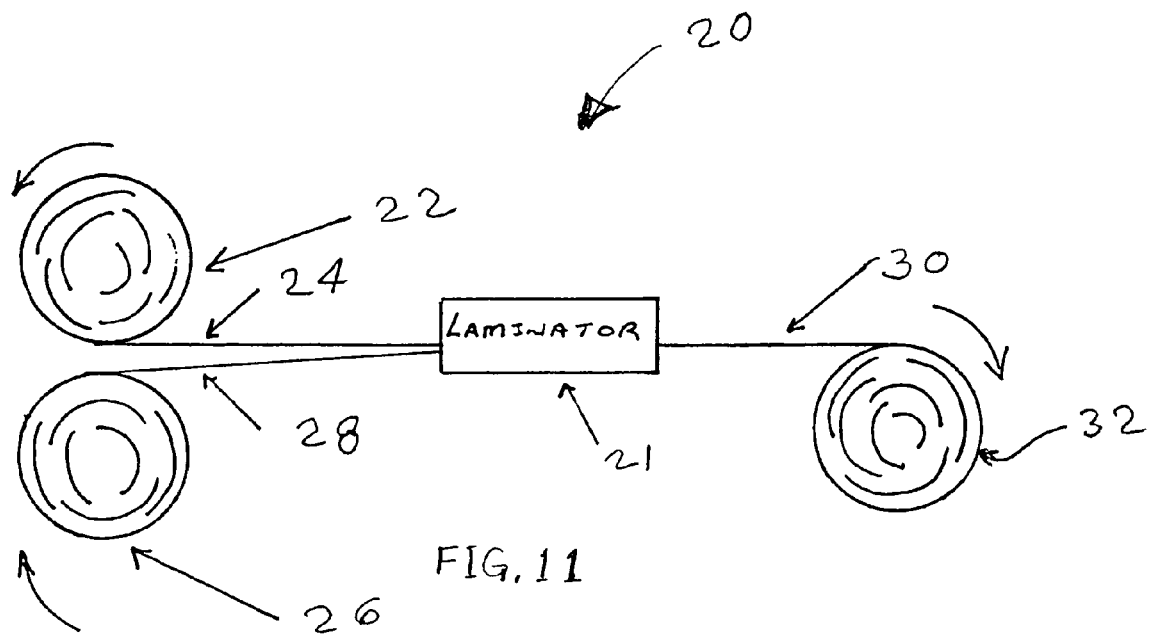

DENTAL APPLIANCE AND METHOD FOR MAKING

CROSS-REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates generally to the field of dentistry and, in particular, to dental appliances.

2. Description of Related Art

Dental appliances such as "invisible" retainers are now in regular use. Such dental appliances are made from a single material which is hard in order to retain its shape and exert sufficient pressure on a user's teeth.

U.S. Pat. No. 4,983,334 to Loren S. Adell shows a multilayer appliance forming a memory material.

BRIEF SUMMARY OF THE INVENTION

A method for making a dental appliance such as a dental retainer, a dental tooth repositioner or a custom bleaching tray according to the present invention includes the step of affixing a first blank piece of material to a second blank piece of material forming a combined blank. The first blank piece of material is substantially softer than the second blank piece of material. The combined blank is then placed over a dental cast with the first blank piece of material faces the dental cast, and a dental appliance is formed by using a thermal form suck-down of the combined blank over the dental cast with the first blank piece of material in contact with the teeth of the dental cast. Finally, the dental appliance is removed from the dental cast. The dental appliance can be trimmed while it is on the dental cast or after it is removed.

There are several methods for affixing a first blank piece of material to a second blank piece of material, including laminating the first blank piece of material to the second blank piece of material, bonding the first blank piece of material to the second blank piece of material, and sealing the first blank piece of material to the second blank piece of material.

In a preferred form of a method according to the present invention, the Durometer hardness range of the first blank piece of material is from about 60 to about 90, preferably from about 80 to about 90, based on a Shore "A" scale, and the Rockwell hardness range of the second blank piece of material is from about 90 to about 115.

A dental appliance according to the present invention, for placement on the teeth of a user includes a first layer, created from the first piece of blank material, for direct contact with the teeth of the user, and a second layer, created from the second piece of blank material, affixed over the first layer. Again, the first layer is substantially softer than the second layer.

The second layer can be affixed to the first layer in several ways, including laminated to the first layer, bonded to the first layer, and sealed to the first layer.

In a preferred form of a dental appliance according to the present invention, the Durometer hardness range of the first layer is from about 60 to about 90, preferably from about 80 to about 90, based on a Shore "A" scale and the Rockwell hardness range of the second layer is from about 90 to about 115.

These and other objects, advantages and features of this invention will be apparent from the following description taken with reference to the accompanying drawing, wherein is shown a preferred embodiment of the invention.

BRIEF DESCRIPTION OF THE SEVERAL VIEWS OF THE DRAWING

FIG. 1 is a top view of a softer piece of blank material;

FIG. 2 is a top view of a harder piece of blank material;

FIG. 3 is a top right perspective view of a softer piece of blank material being sealed to a harder piece of blank material;

FIG. 4 is a cross-sectional view of a softer piece of blank material affixed to a harder piece of blank material;

FIG. 5 is a right front perspective view of the softer piece of blank material affixed to the harder piece of blank material of FIG. 4;

FIG. 6 is a right front perspective view of a softer piece of blank material affixed to a harder piece of blank material that has been formed over a dental cast;

FIG. 9 is a cross-sectional view of an alternative embodiment of a softer piece of blank material affixed to a harder piece of blank material;

FIG. 10 is a cross-sectional view of another alternative embodiment of a softer piece of blank material affixed to a harder piece of blank material;

FIG. 11 is a schematic representation of a softer blank material being laminated to harder blank material;

DETAILED DESCRIPTION OF THE INVENTION

Figure 7:
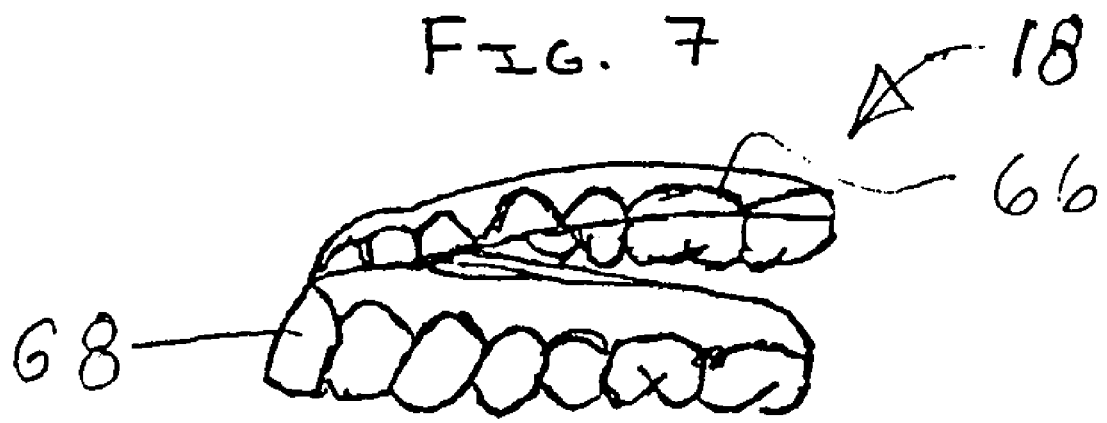
FIG. 7 is a top right perspective view of a dental appliance according to the present invention.

Referring now to the drawing, and in particular to FIGS. 1 through 4, a method for making a dental appliance such as a dental retainer, a dental tooth repositioner or a custom bleaching tray according to the present invention includes the step of affixing a first blank piece of material 10 to a second blank piece of material 12 forming a combined blank 14. One form of affixing is putting an adhesive backing on first blank piece of material 10 and smoothing it onto second blank piece of material 12 as shown in FIG. 3. Such a method can be performed by hand using individual pieces of blank materials. First blank piece of material 10 is substantially softer than second blank piece of material 12. Typically, first blank piece of material 10 has a thickness from about 0.005 inches to about 0.018 inches, and the second blank piece of material has a thickness from about 0.020 inches to about 0.040 inches, and preferably from about 0.025 inches to about 0.030 inches. Although the pieces of blank materials are shown as square, they could come in any number of shapes.

Figure 8:
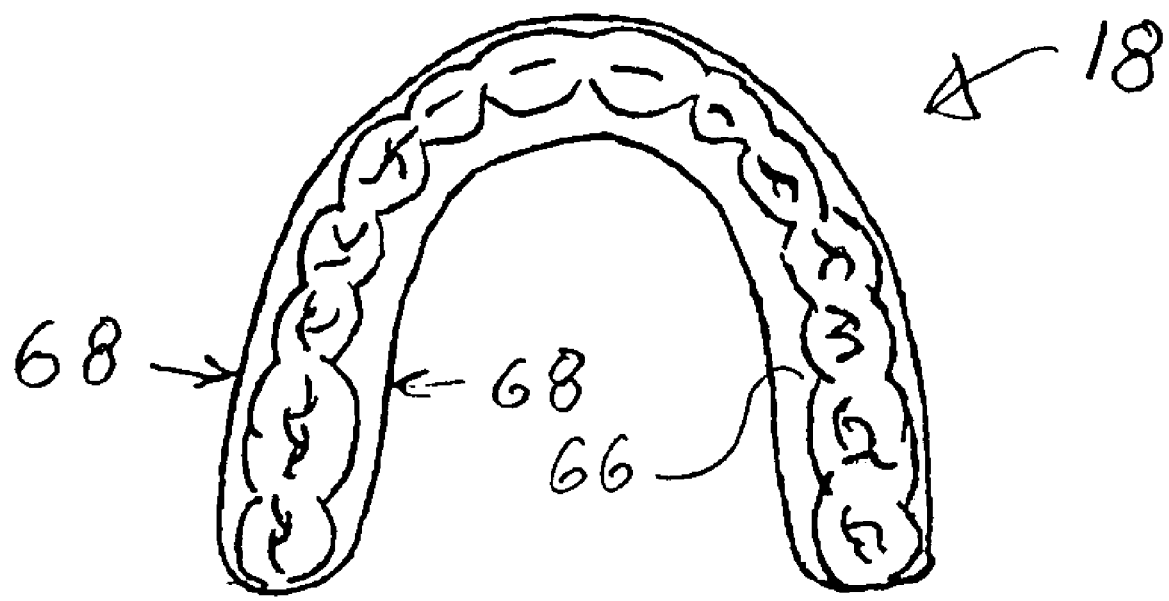
FIG. 8 is a top view of the dental appliance of FIG. 7.
Figure 12:
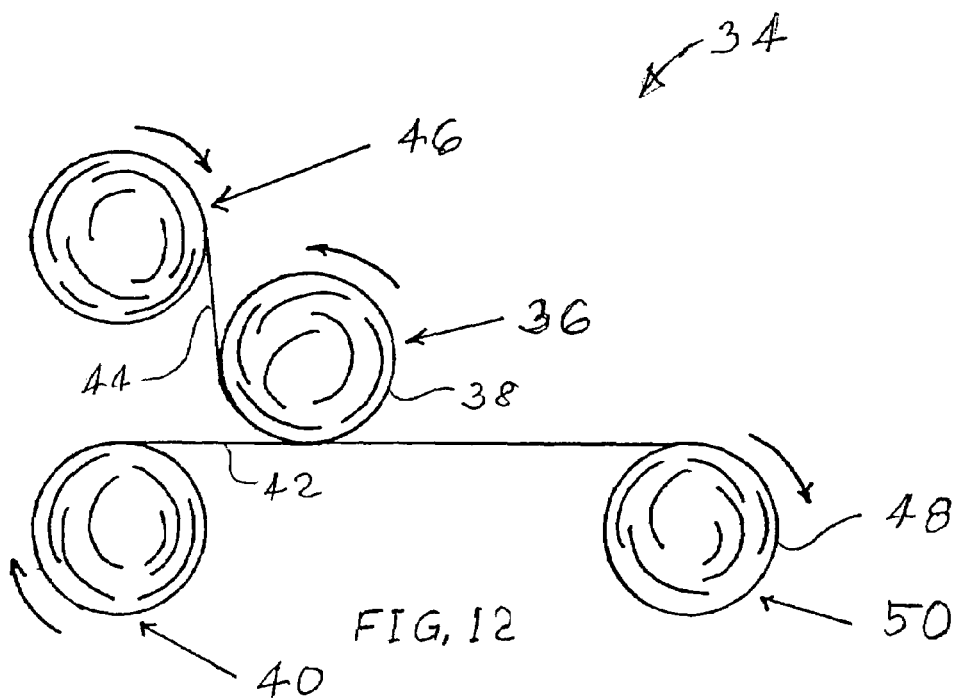
FIG. 12 is a schematic representation of a softer blank material being bonded to harder blank material by a double sided adhesive.
Figure 13:
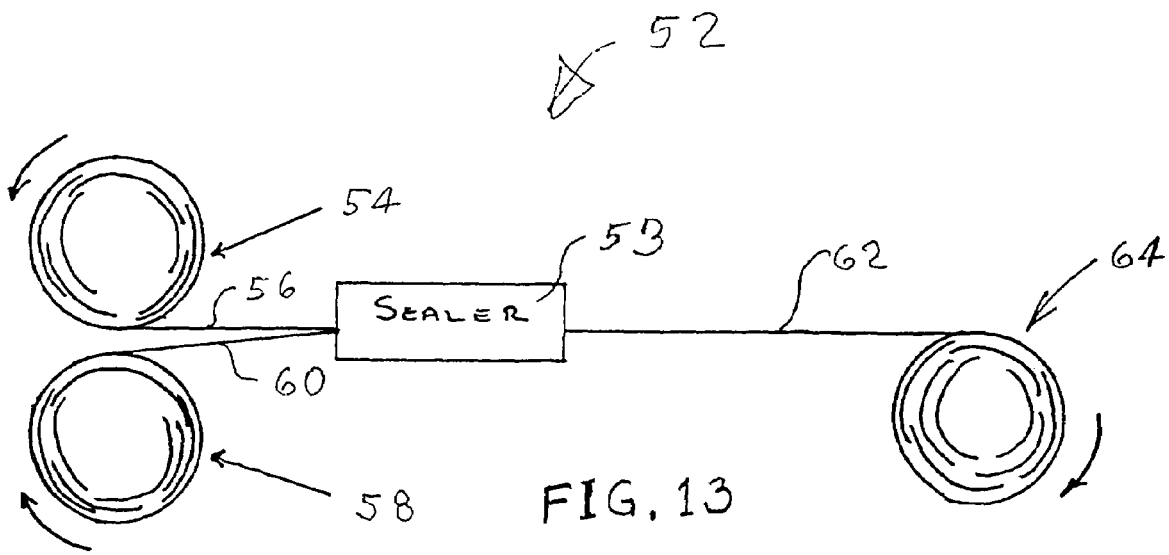
FIG. 13 is a schematic representation of a softer blank material being sealed to harder blank material.

Referring also to FIGS. 5 and 6, combined blank 14 is then placed over a dental cast 16, as shown in FIG. 6, with the first blank piece of material faces the dental cast, and a dental appliance is formed by using a thermal form suckdown of the combined blank over the dental cast with the first blank piece of material in contact with the teeth of the dental cast. In this way, the soft portion of the material will be in contact with a user's teeth. In one embodiment, the softer material also creates a slight stickiness or gumminess. Referring now to FIGS. 7 and 8, the dental appliance 18 is removed from the dental cast. The dental appliance can be trimmed while it is on the dental cast or after it is removed.

Referring now to FIGS. 9 through 13, there are several methods for affixing a first blank piece of material to a second blank piece of material, including laminating 20 with a laminator 21 the first blank piece of material from a roll 22 of first blank material 24 to the second blank piece of material from a roll 26 of the second blank material 28 into a combined blank material 30 which is wound to a roll 32. Typically, first blank material 24 for this arrangement is semi-hard and in thickness from about 0.012 inches to about 0.015 inches. The second blank material 28 is hard, with thickness typically from about 0.020 inches to about 0.040 inches and preferably from about 0.025 inches to about 0.030 inches.

Another method for affixing is bonding 34 the first blank piece of material from a roll 36 of first blank material 38 to the second blank piece of material from a roll 40 of second blank material 42 using a double sided adhesive 44 from a roll 46 into a combined blank material 48 which is wound onto a roll 50. Typically, first blank material 38 for this arrangement is semi-hard and in thickness from about 0.012 inches to about 0.015 inches. The second blank material 42 is hard, with thickness typically from about 0.020 inches to about 0.040 inches, preferably from about 0.025 inches to about 0.030 inches, and the adhesive material 44 is from about 0.005 inches to about 0.008 inches. In one method using adhesive, the adhesive can be applied to either the first material or to the second material and backed by a release paper or other release material. When ready to use, the release paper or other release material is simply pulled off, exposing the adhesive. Referring still to the process of FIG. 12, in such an arrangement, first blank material 38 or second blank material 42 can be replaced by the release material.

Yet another way of affixing is by sealing 52 with a sealer 53 the first blank piece of material from a roll 54 of first blank material 56 to the second blank piece of material from a roll 58 of second blank material 60 into a combined blank material 62 which is wound onto a roll 64.

In a preferred form of a method according to the present invention, the Durometer hardness range of the first blank piece of material is from about 60 to about 90, preferably from about 80 to about 90, based on a Shore "A" scale, and the Rockwell hardness range of the second blank piece of material is from about 90 to about 115.

Referring again to FIGS. 7 and 8, a dental appliance 18 according to the present invention, for placement on the teeth of a user includes a first layer 66, created from first piece of blank material 10, for direct contact with the teeth of the user, and a second layer 68, created from second piece of blank material 12, affixed over the first layer. Again, the first layer is substantially softer than the second layer.

The second layer can be affixed to the first layer in several ways, including laminated to the first layer, bonded to the first layer, and sealed to the first layer.

In a preferred form of a dental appliance according to the present invention, the Durometer hardness range of the first layer is from about 60 to about 90, preferably from about 80 to about 90, based on a Shore "A" scale and the Rockwell hardness range of the second layer is from about 90 to about 115.

Either or both the first layer or the second layer can comprise a memory material, which could include memory fiber.

From the foregoing it will be seen that this invention is well adapted to attain all of the ends and objectives hereinabove set forth, together with other advantages which are inherent to the apparatus.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the figures of the accompanying drawings is to be interpreted as illustrative and not in a limiting sense.

The invention claimed is:

1. A method for making a dental appliance, comprising in combination the steps of:
   affixing a first blank piece of material to a second blank piece of material forming a combined blank, wherein the first blank piece of material is substantially softer than the second blank piece of material;
   placing the combined blank over a dental cast with the first blank piece of material faces the dental cast;
   forming the combined blank over the dental cast with the first blank piece of material in contact with the teeth of the dental cast, creating a dental appliance;
   removing the dental appliance from the dental cast;
   applying a layer of adhesive to either the first blank piece of material or the second blank piece of material; and
   applying release material to the layer of adhesive material, wherein the release material can be removed from the adhesive material when affixing the first blank piece of material to the second blank piece of material forming a combined blank.

2. A dental appliance made by the process of claim 1.

3. A method according to claim 1 wherein affixing a first blank piece of material to a second blank piece of material comprises laminating the first blank piece of material to the second blank piece of material.

4. A method according to claim 1 wherein affixing a first blank piece of material to a second blank piece of material comprises bonding the first blank piece of material to the second blank piece of material.

5. A method according to claim 1 wherein affixing a first blank piece of material to a second blank piece of material comprises sealing the first blank piece of material to the second blank piece of material.

6. A method according to claim 1 wherein the Durometer hardness range of the first blank piece of material is from about 60 to about 90, based on a Shore "A" scale, and the Rockwell hardness range of the second blank piece of material is from about 90 to about 115.

7. A method according to claim 1 wherein the Durometer hardness range of the first blank piece of material is from about 80 to about 90, based on a Shore "A" scale, and the Rockwell hardness range of the second blank piece of material is from about 90 to about 115.

8. A method according to claim 1 wherein the thickness of the first blank piece of material is from about 0.012 inches to about 0.015 inches, and the thickness of the second blank piece of material is from about 0.020 inches to about 0.040 inches.

9. A method according to claim 1 wherein the thickness of the first blank piece of material is from about 0.012 inches to about 0.015 inches, and the thickness of the second blank piece of material is from about 0.025 inches to about 0.030 inches.

10. A method according to claim 1 wherein affixing a first blank piece of material to a second blank piece of material comprises the steps of:
   laminating a roll of the first blank piece of material to a roll of the second blank piece of material;
   forming a roll of the laminated first and second blank material; and cutting the laminated roll into individual blanks.

11. A method according to claim 1 wherein affixing a first blank piece of material to a second blank piece of material comprises the steps of:
   bonding a roll of the first blank piece of material to a roll of the second blank piece of material;
   forming a roll of the bonded first and second blank material; and
   cutting the bonded roll into individual blanks.

12. A method according to claim 1 wherein affixing a first blank piece of material to a second blank piece of material comprises the steps of:
   sealing a roll of the first blank piece of material to a roll of the second blank piece of material;
   forming a roll of the sealed first and second blank material; and
   cutting the sealed roll into individual blanks.

* * * * *